US012779078B2

(12) United States Patent
Machida et al.

(10) Patent No.: US 12,779,078 B2
(45) Date of Patent: Nov. 3, 2026

(54) AROMA CHEMICAL PRESENTATION APPARATUS

(71) Applicant: Sony Interactive Entertainment Inc., Tokyo (JP)

(72) Inventors: Yuichi Machida, Kanagawa (JP); Shinichi Hirata, Kanagawa (JP); Takeshi Asano, Tokyo (JP); Yoichi Nishimaki, Kanagawa (JP); Takao Maruyama, Kanagawa (JP); Yumi Ueda, Chiba (JP)

(73) Assignee: Sony Interactive Entertainment Inc., Tokyo (JP)

( * ) Notice: Subject to any disclaimer, the term of this patent is extended or adjusted under 35 U.S.C. 154(b) by 498 days.

(21) Appl. No.: 18/248,560

(22) PCT Filed: Oct. 19, 2020

(86) PCT No.: PCT/JP2020/039303

§ 371 (c)(1),
(2) Date: Apr. 11, 2023

(87) PCT Pub. No.: WO2022/085056

PCT Pub. Date: Apr. 28, 2022

(65) Prior Publication Data

US 2023/0372570 A1 Nov. 23, 2023

(51) Int. Cl.
*A61L 9/12* (2006.01)
*A63F 13/28* (2014.01)

(52) U.S. Cl.
CPC .............. *A61L 9/122* (2013.01); *A63F 13/28* (2014.09)

(58) Field of Classification Search
CPC ........... A61L 9/122; A61L 9/125; A63F 13/28
See application file for complete search history.

(56) References Cited

U.S. PATENT DOCUMENTS 5,005,820 A * 4/1991 Leemhuis ................ B65H 1/20 271/127

FOREIGN PATENT DOCUMENTS

| | | | | | |
|---|---|---|---|---|---|
| CA | 2343256 | A1 * | 3/2000 | ............. | A61L 9/125 |
| JP | 09327506 | A | 12/1997 | | |
| JP | 1085315 | A | 4/1998 | | |
| JP | 11508466 | A | 7/1999 | | |
| JP | 3670764 | B2 * | 7/2005 | | |
| JP | 2007130255 | A | 5/2007 | | |
| JP | 2009265453 | A | 11/2009 | | |
| JP | 2020162923 | A | 10/2020 | | |

OTHER PUBLICATIONS

Machined translation of JP 3670764 (Year: 2005).*
Machine language of JP 2020162923 (Year: 2020).*
International Search Report for corresponding PCT Application No. PCT/JP2020/039303, 6 pages, dated Dec. 15, 2020.

* cited by examiner

*Primary Examiner* — Timothy C Cleveland
(74) *Attorney, Agent, or Firm* — Kilpatrick Townsend & Stockton LLP

(57) ABSTRACT

An aroma chemical presentation apparatus includes an encapsulation body supporting unit that supports an aroma chemical encapsulation body in which an aroma chemical material is encapsulated, an action body that is brought into contact with the aroma chemical encapsulation body to cause the aroma chemical material in the aroma chemical encapsulation body to be emitted, and a derivation fan that forms an air flow in a predetermined direction for deriving the emitted aroma chemical material.

17 Claims, 5 Drawing Sheets

(a)

(b)

(a)

(b)

AROMA CHEMICAL PRESENTATION APPARATUS

TECHNICAL FIELD

The present technology relates to an aroma chemical presentation apparatus.

BACKGROUND ART

In recent years, various aroma chemical presentation devices have been devised. For example, an aroma chemical presentation device in which a liquid aroma chemical is encapsulated in an aroma chemical cartridge and the cartridge is heated to vaporize the liquefied aroma chemical to present its odor is available.

SUMMARY

Technical Problem

In the meantime, in recent years, there has been developed a technology in which an encapsulation body in which an aroma chemical is encapsulated in a microcapsule or the like is used such that the encapsulation body is fixed to and used with a sheet-like medium or the like. Although such a medium as just described is easy and simple in handling, it has not been devised in the current state to mechanically present an aroma chemical.

The present invention has been made taking the actual situation described above into consideration, and it is one of objects of the present invention to provide an aroma chemical presentation apparatus that can perform aroma chemical presentation using an encapsulation body.

Solution to Problem

One mode of the present invention for solving the problem of the conventional example described above is an aroma chemical presentation apparatus including an encapsulation body supporting unit that supports an aroma chemical encapsulation body in which an aroma chemical material is encapsulated, an action body that physically acts upon the aroma chemical encapsulation body to cause the aroma chemical material in the aroma chemical encapsulation body to be emitted, and a derivation fan that forms an air flow in a predetermined direction for deriving the emitted aroma chemical material.

Advantageous Effect of Invention

With the aroma chemical presentation apparatus according to the one mode of the present invention, it is possible to perform aroma chemical presentation using an encapsulation body.

DESCRIPTION OF EMBODIMENT

Figure 1:
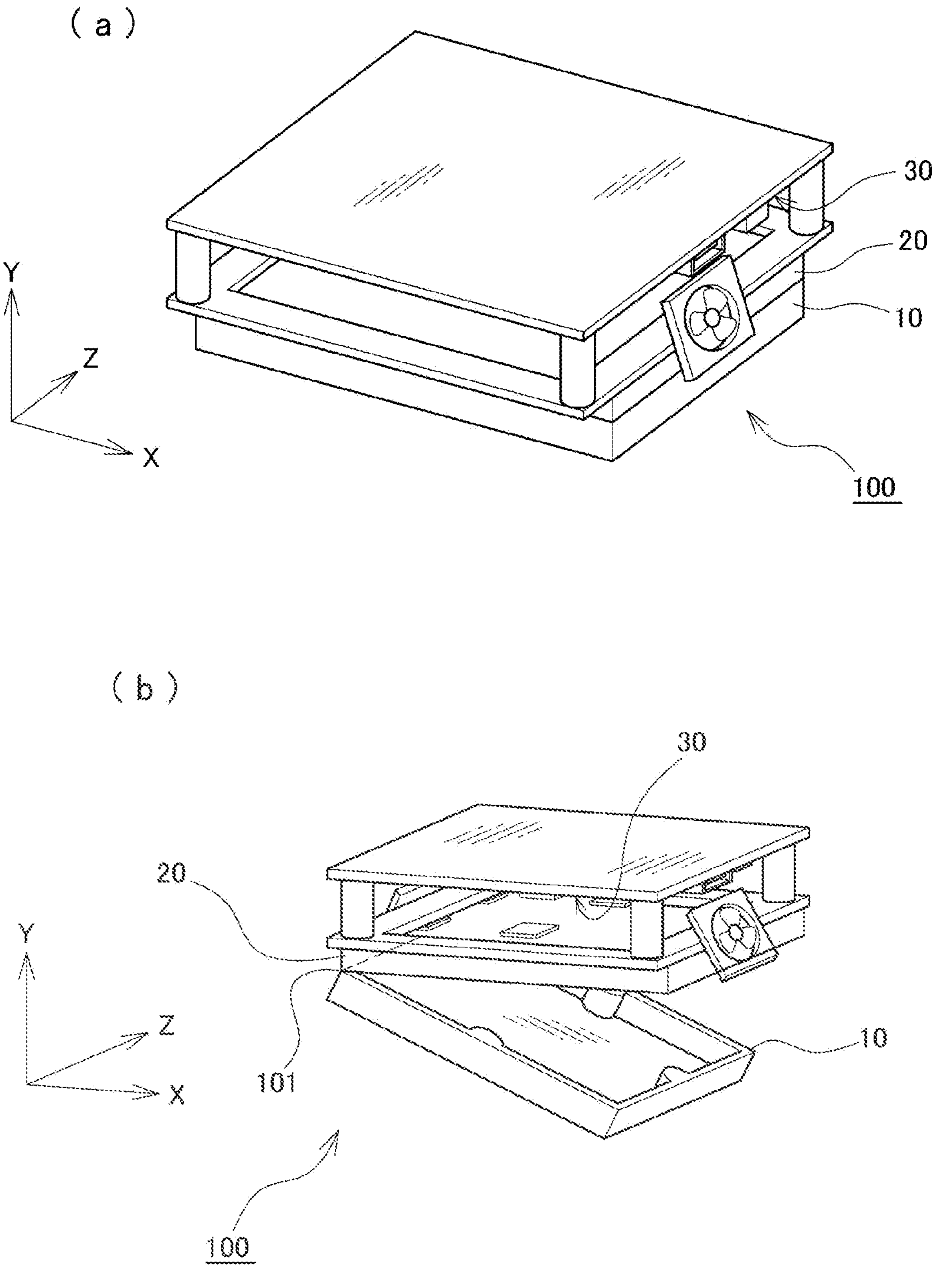
FIGS. 1(*a*) and 1(*b*) are perspective views depicting a general configuration of an aroma chemical presentation apparatus according to an embodiment of the present invention.

An embodiment of the present invention is described with reference to the drawings. An aroma chemical presentation apparatus 100 according to the embodiment of the present invention is connected to and used together with an information processing apparatus such as a game machine for home use or a personal computer and includes a tray unit 10, a mechanism unit 20, and a control circuit unit 30 as exemplified in FIGS. 1(*a*) and 2(*b*). It is to be noted that, in the drawings, any size, any ratio, and so forth are for the explanation and can be altered suitably when the present invention is carried out.

The tray unit 10 is connected to a side face of the mechanism unit 20 through a hinge 101 as exemplified in FIGS. 1(*a*) and 2(*b*) such that, when side faces on the sides of the mechanism unit 20 and the tray unit 10, the side faces being opposed to the hinge 101, are placed into a closed state, the mechanism unit 20 and the tray unit 10 are integrated with each other to form a container body (FIG. 1(*a*)) and the entirety from the tray unit 10 to the mechanism unit 20 represents a columnar shape. In the following description, in the drawings, the positive direction of the Y axis is an upper direction, and the negative direction of the Y axis is a lower direction.

In addition, when the hinge 101 is opened (FIG. 1(*b*)), the side faces on the sides of the mechanism unit 20 and the tray unit 10, the side faces being opposed to the hinge 101, are placed into an open state, in which access to the inside of the tray unit 10 is possible.

Figure 2:
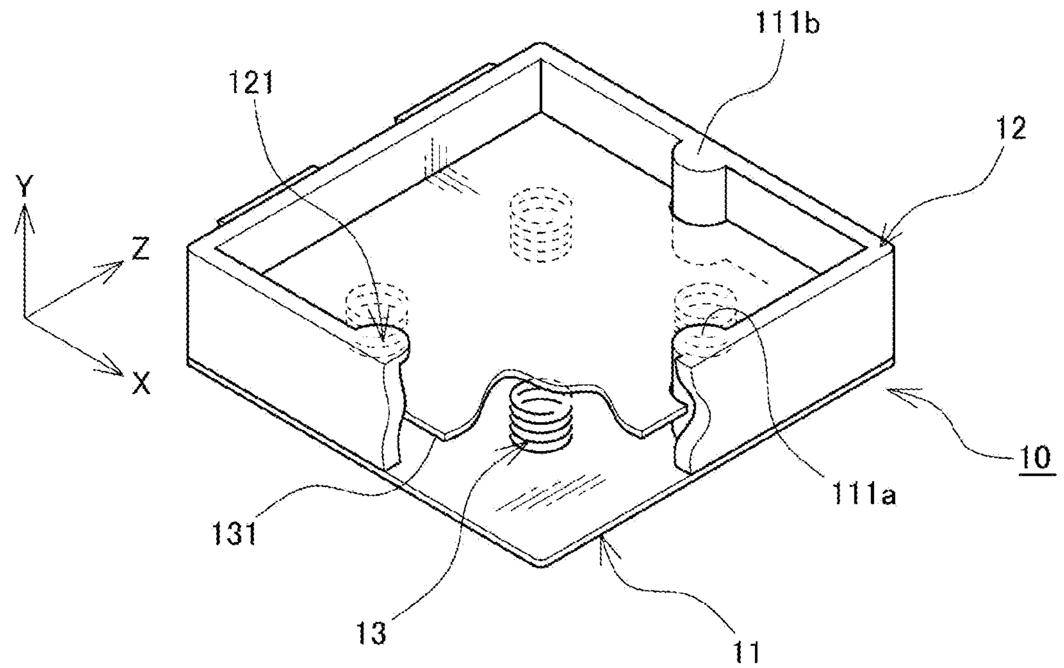
FIG. 2 is an explanatory view depicting a configuration of a tray unit provided in the aroma chemical presentation apparatus according to the embodiment of the present invention.

The tray unit 10 in the present embodiment functions as an encapsulation body supporting unit and includes, as depicted in FIG. 2 in which a state of the tray unit 10 partly broken is exemplified, a bottom portion 11 of a substantially rectangular shape, a wall portion 12 formed on a peripheral edge portion of the bottom portion 11, and a biasing unit 13. The biasing unit 13 substantially includes a sheet-like pressing body 131 having a shape same as that of the inner periphery of the bottom portion 11 surrounded by the wall portion 12, and an elastic body 132 that is interposed between the pressing body 131 and the bottom portion 11 and biases the pressing body 131 to the mechanism unit 20 side.

Further, in an example of the present embodiment, a projection projecting toward the inner side of the tray unit 10 may be formed at part of the wall portion 12 of the tray unit 10 such that the pressing body 131 is prevented from coming off from the tray unit 10.

Figure 3:
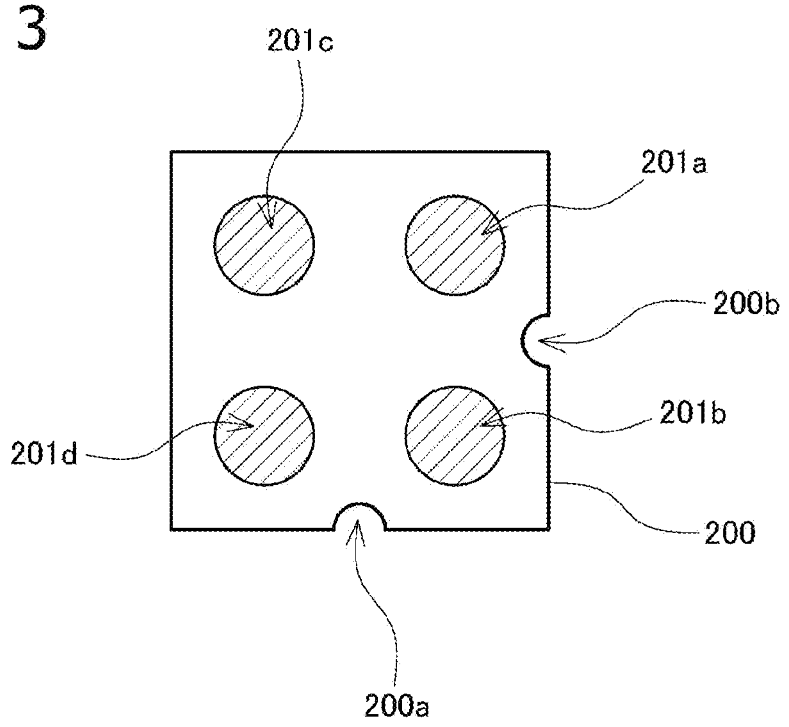
FIG. 3 is an explanatory view depicting an example of an aroma chemical carrier that is to be set to the aroma chemical presentation apparatus according to the embodiment of the present invention.

In an example of the present embodiment, such an aroma chemical carrier 200 as exemplified in FIG. 3 is accommodated into the tray unit 10. Although the aroma chemical carrier 200 has a form of a sheet and has a substantially rectangular shape, it may have cutouts 200*a*, 200*b*, . . . formed at asymmetrical positions thereof.

Further, on the surface side of the aroma chemical carrier 200, microcapsules in which aroma chemicals are encapsulated are fixed in at least one layer (typically, layered in multiple layers). In the example in FIG. 3, depicted is an example in which layers (hereinafter referred to as aroma chemical fixation portions) 201*a*, 201*b*, . . . of microcapsules in which the aroma chemicals are encapsulated are formed in a disk shape. However, this formation example is one example and is not restrictive. Further, the types of aroma chemicals encapsulated in the aroma chemical fixation portions 201*a*, 201*b*, . . . formed at the locations mentioned may be different from each other or may be the same as each other.

Such fixation of the microcapsules to the aroma chemical carrier 200 may be performed by a widely known method such as application of the microcapsules to the aroma chemical carrier 200 together with adhesive.

The bottom portion 11 of the tray unit 10 of the aroma chemical presentation apparatus 100 of the present embodiment may have engaging projections 111 formed thereon for engaging with the cutouts 200*a*, 200*b*, . . . of the aroma chemical carrier 200. In this case, the pressing body 131 has a shape avoiding the engaging projections 111. Consequently, upper portions of the engaging projections 111 come to a position nearer to the mechanism unit 20 side than the pressing body 131, and when the aroma chemical carrier 200 is accommodated into the tray unit 10, the aroma chemical carrier 200 is prevented from being accommodated with the front and back or the direction thereof mistaken, because the cutouts 200*a*, 200*b*, . . . formed asymmetrically thereon are disposed in such a manner as to engage with the respective corresponding engaging projections 111.

Figure 4:
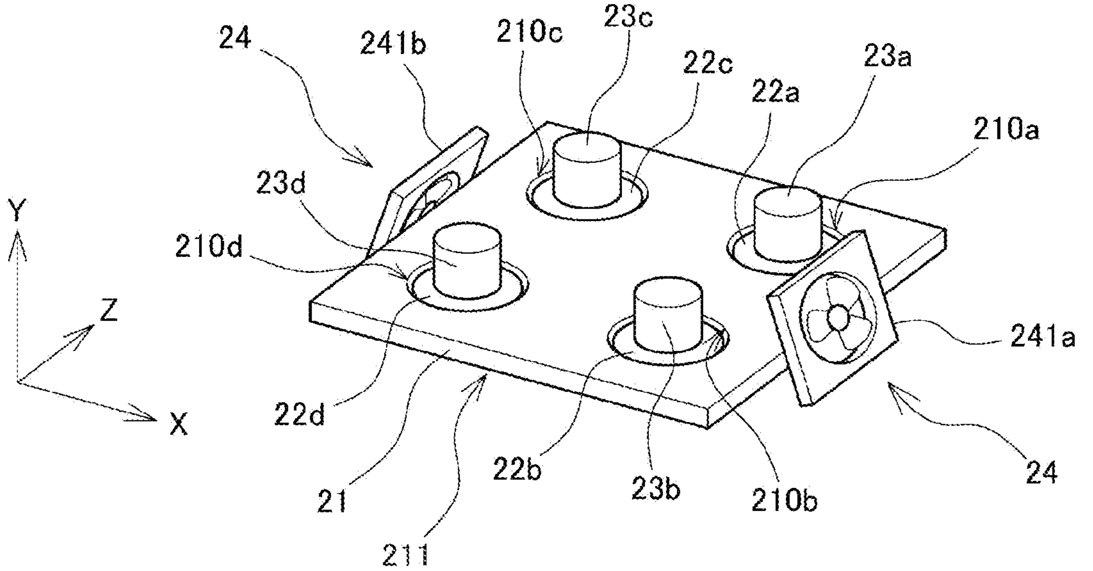
FIGS. 4(*a*) and 4(*b*) are general explanatory views depicting an example of a configuration of a mechanism unit of the aroma chemical presentation apparatus according to the embodiment of the present invention.
Figure 4:
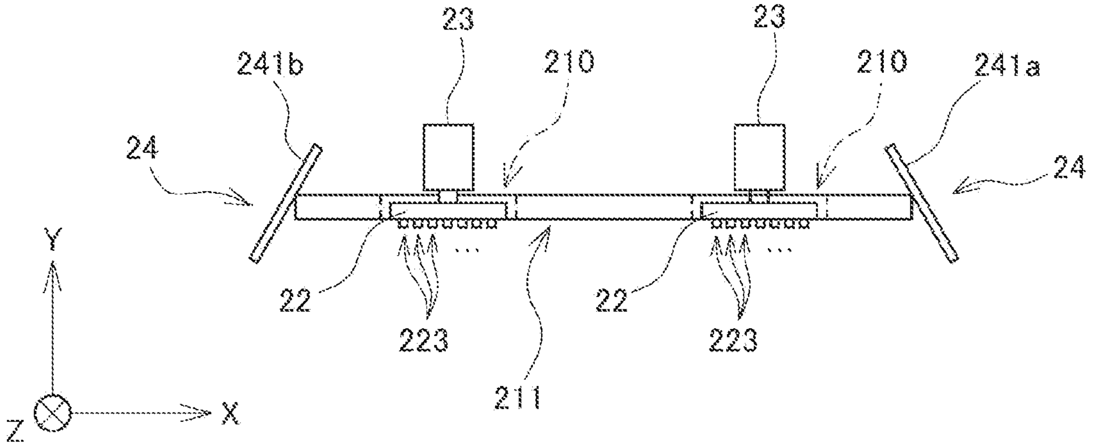

A configuration of the mechanism unit 20 is depicted in FIGS. 4(*a*) and 4(*b*). As exemplified in FIG. 4(*a*), the mechanism unit 20 includes a mechanism unit housing 21, action portions 22*a*, 22*b*, . . . whose number corresponds to the number of the aroma chemical fixation portions 201*a*, 201*b*, . . . formed on the aroma chemical carrier 200, driving units 23*a*, 23*b*, . . . that drive the action portions 22*a*, 22*b*, . . . , respectively, and an air flow controlling unit 24.

The mechanism unit housing 21 has a bottom portion 211 in which openings 210*a*, 210*b*, into which the action portions 22*a*, 22*b*, . . . are to be inserted are formed, and supports the driving units 23 and the air flow controlling unit 24 above the bottom face of the bottom portion 211.

Figure 5:
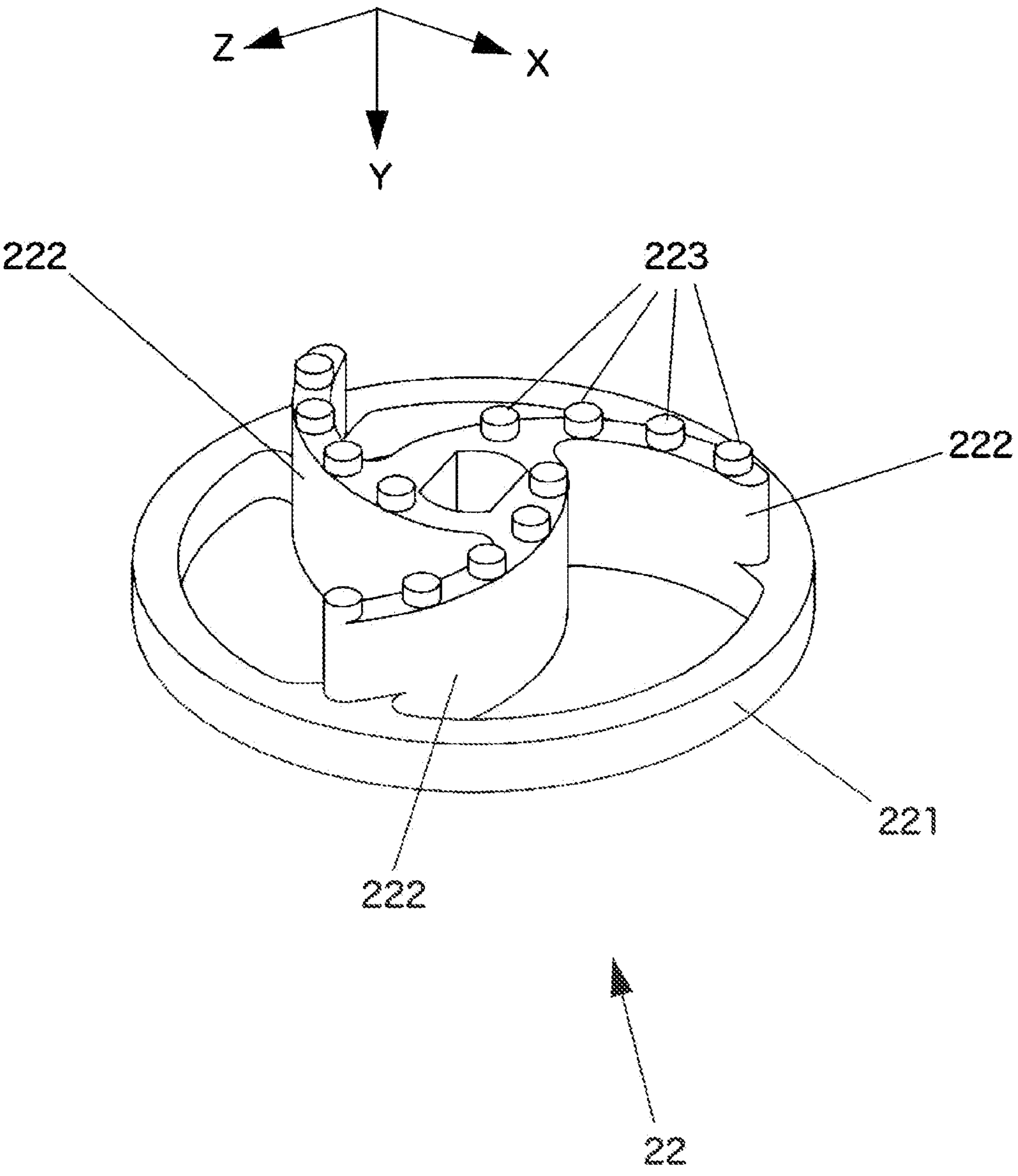
FIG. 5 is an explanatory view depicting an example of a configuration of an action portion provided in the aroma chemical presentation apparatus according to the embodiment of the present invention.
Figure 6:
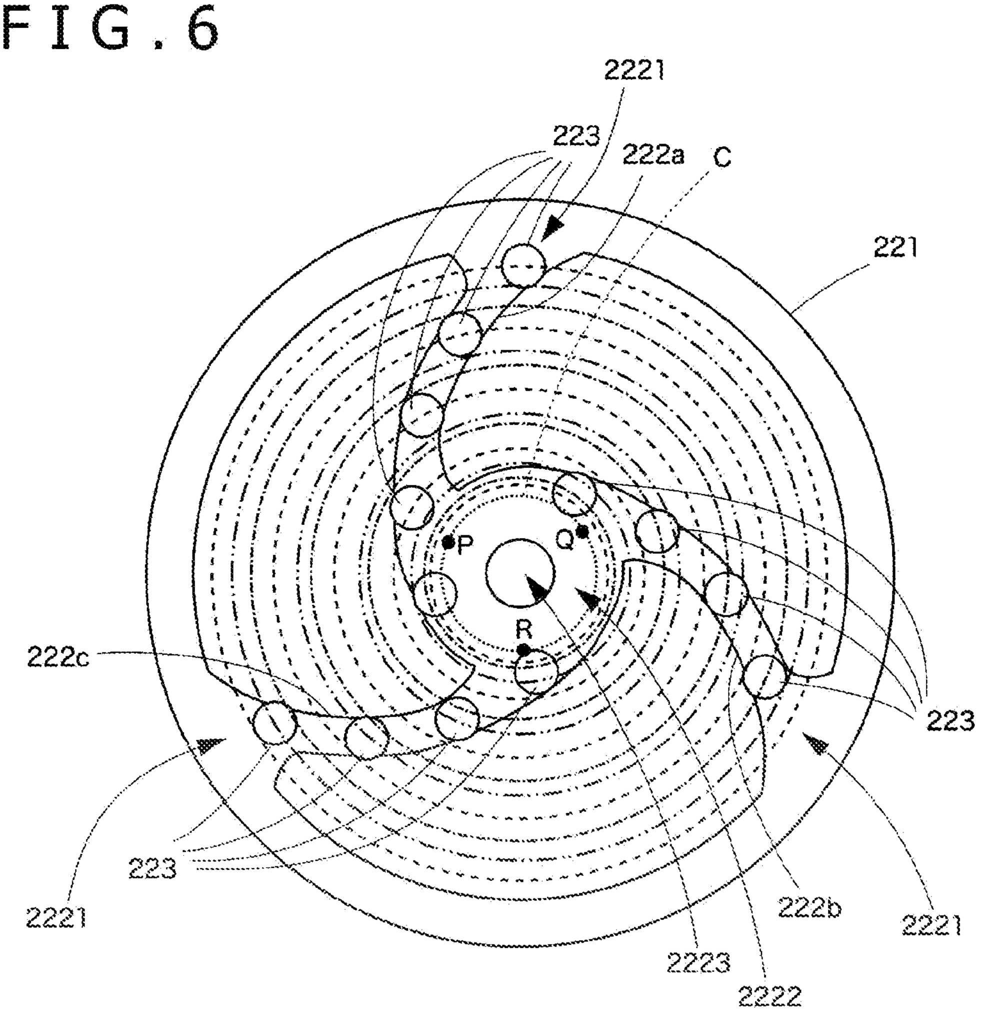
FIG. 6 is an explanatory view depicting an example of a configuration and operation of the action portion provided in the aroma chemical presentation apparatus according to the embodiment of the present invention.

Each action portion 22 (in the following description, for a configuration common to the action portions 22*a*, 22*b*, . . . , the reference sign is described with an added alphabetical letter omitted like the action portion 22) includes a ring-shaped outer circumferential portion 221 as exemplified in FIGS. 5 and 6.

Further, on the outer circumferential portion 221, a plurality of spoke bodies 222*a*, 222*b*, (in the following description, when there is no necessity to distinguish any of them, it is referred to as a spoke body 222) are formed integrally such that they extend radially or in radiation curves, the spoke bodies 222 having starting points at points in the proximity of the center of the outer circumferential portion 221 (for example, as exemplified in FIG. 6, the center point of the outer circumferential portion 221 or a plurality of points P, Q, and R at equal distances in a circumferential direction on a virtual circle C which is coaxial with the outer circumferential portion 221 and which has a radius smaller than that of the outer circumferential portion 221) and each being fixed at a terminal end side end portion thereof to the outer circumferential portion 221. Further, a plurality of columnar (in the example of FIGS. 5 and 6, cylindrical) protrusions 223 are provided on a lower face (the tray unit 10 side) of the spoke bodies 222.

It is to be noted that each spoke body 222 may be in a state in which it extends farther than the outer circumferential portion 221 in the height direction (Y axis direction), and the head portion of each protrusion 223 (which is a downward top portion and which is the side contacting with the aroma chemical carrier 200 as hereinafter described) may be rounded in such a manner as to have no angular portion. Further, the diameter of the outer circumferential portion 221 is made same as the diameter of the disk-shaped aroma chemical fixation portion 201 formed on the aroma chemical carrier 200.

Each protrusion 223 of the action portion 22 protrudes toward the tray unit 10 farther than the bottom portion of the opening 210 of the mechanism unit housing 21 (FIG. 4(*b*)). When the aroma chemical carrier 200 is accommodated into the tray unit 10 and the tray unit 10 is closed, the protrusion 223 is brought into contact with the aroma chemical fixation portion 201 of the aroma chemical carrier 200 at the corresponding position. In particular, in the present embodiment, the action portion 22 that includes the protrusion 223 corresponds to an action body.

The spoke bodies 222 are connected at outer side end portions 2221 thereof to the outer circumferential portion 221 and connected at inner side end portions thereof to each other to form a center body 2222. Further, the protrusions 223 formed on the spoke bodies 222 are preferably disposed such that, when the outer circumferential portion 221 rotates around the center thereof, the loci of movement of the protrusions do not overlap with each other (FIG. 6). It is to be noted that, in FIG. 6, the loci of movement of the protrusions 223 on the spoke body 222*a* are indicated by broken lines, the loci of movement of the protrusions 223 on the spoke body 222*b* are indicated by alternate long and short dash lines, and the loci of movement of the protrusions 223 on the spoke body 222*c* are indicated by alternate long and two short dashes lines.

Each driving unit 23 (for a configuration common to the driving units 23*a*, 23*b*, . . . , the reference sign is described with an added alphabetical letter omitted like driving unit 23) includes a rotary actuator such as a motor. The axis of rotation of the driving unit 23 is connected to the center of the outer circumferential portion 221 of the action portion 22 and drives the outer circumferential portion 221 of the action portion 22 to rotate. In particular, in the example in FIG. 5, since the plurality of spoke bodies 222 extend to the proximity of the center of the outer circumferential portion 221, the rotary shaft of the driving unit 23 is fixed to the center of the center body 2222 formed by the spoke bodies 22, that is, to a position 2223 that corresponds to the center of the outer circumferential portion 221.

In an example of the present embodiment, the driving unit 23 includes a stepping motor, and drives the outer circumferential portion 221 of the action portion 22 to rotate, according to an instruction inputted from the control circuit unit 30 hereinafter described. A method of control of this rotation is hereinafter described.

The air flow controlling unit 24 includes a derivation fan 241*a* and an exhaust fan 241*b* paired with each other and disposed on two sides of the mechanism unit housing 21 that are opposed to each other. The derivation fan 241*a* derives vaporized aroma chemical which is emitted in the tray unit 10 and flows out through the openings 210*a*, 210*b*, . . . of the mechanism unit housing 21, in a predetermined direction, for example, to the outer side of the mechanism unit housing 21. Meanwhile, the exhaust fan 241*b* derives vaporized aroma chemical which flows out through the openings 210*a*, 210*b*, . . . of the mechanism unit housing 21, in a direction different from the predetermined direction described above, for example, in a direction different from the derivation fan 241*a* to the outer side of the mechanism unit housing 21.

In the example exemplified in FIGS. 4(*a*) and 4(*b*), since the derivation fan 241*a* and the exhaust fan 241*b* are disposed at positions opposed to each other across the mechanism unit housing 21, the derivation fan 241*a* and the exhaust fan 241*b* generate air flows in the opposite directions to each other. In an example of the present embodiment, the derivation fan 241*a* generates an air flow directed in a direction to the nose of a user while the exhaust fan 241*b* generates an air flow directed in a direction away from the nose of the user.

It is to be noted that the reason why the exhaust fan 241*b* that generates an air flow directed in the direction away from the nose of the user is that it is intended to swiftly remove, in a case where the aroma chemical to be presented is to be switched or in a case where presentation of an aroma chemical is to be ended, the component of the aroma chemical having been presented until the current point of time, from the nose of the user. However, in a case where this is not necessary, the exhaust fan 241*b* that generates an air flow in the direction away from the nose of the user is not necessarily required.

Now, an example of rotation control of the driving unit 23 by the control circuit unit 30 is described. The control circuit unit 30 includes a microcomputer and so forth and operates according to a program stored in the inside thereof. The control circuit unit 30 is connected to the information processing apparatus by wired or wireless connection, accepts, from the information processing apparatus, input of information that specifies a driving unit 23*a*, 23*b*, . . . to be rotated and information designating an intensity of odor of the aroma chemical to be emitted, and controls the driving unit 23*a*, 23*b*, . . . specified by the information, to rotate by a predetermined method.

Here, the information that specifies an intensity of odor of the aroma chemical designates duration of rotation, the number of times of rotation, or the like, and the control circuit unit 30 repeats a reciprocating rotary motion of rotating the specified driving unit 23*a*, 23*b*, . . . by F degrees in a predetermined direction and then rotating the specified driving unit 23*a*, 23*b*, . . . by B degrees in a direction opposite to the predetermined direction, for the designated duration or by the designated number of times of rotation. The control circuit unit 30 thereby causes the protrusions 223 of the action portion 22 that is the action body to move relative to the aroma chemical carrier 200 and the tray unit 10 that supports the aroma chemical carrier 200, such that the protrusions 223 grind the microcapsules of the aroma chemical formed on the aroma chemical carrier 200, to allow the aroma chemical to be emitted.

Note that $F>B>0$ (it is to be noted that any of F and B need not be an integer) is assumed, and by a single time reciprocating rotary motion, the driving unit 23*a*, 23*b*, . . . is placed into a state in which it is rotated by $F-B$ degrees in the predetermined direction described above. This makes it possible to prevent the same place to be ground many times. As an example, $F=5$ degrees and $B=4$ degrees are assumed, and the predetermined direction is a direction in which the driving unit 23 is assumed to rotate in the clockwise direction when it is viewed from below. Further, the reciprocating rotary motion is performed four times per one second (four reciprocations).

[Operation] The present embodiment has such a configuration as described above and operates in the following manner. The aroma chemical presentation apparatus 100 of the present embodiment is attached, for example, to an HMD (head-mounted display) that is to be mounted on the head of the user, and the orientation thereof is set such that the nose of the user is positioned on the downstream side of an air flow generated by the derivation fan 241*a*. Further, the aroma chemical presentation apparatus 100 is connected to the information processing apparatus such as a game machine for home use.

The user opens the hinge 101 that connects the mechanism unit 20 and the tray unit 10 to each other and places the aroma chemical carrier 200 prepared in advance on the pressing body 131 in the tray unit 10. It is to be noted that, in the present example, aroma chemicals different in odor from each other are assumed to be individually fixed to the aroma chemical fixation portions 201*a*, 201*b*, . . . formed on the aroma chemical carrier 200, and which type of aroma chemical is fixed to each of the aroma chemical fixation portions 201*a*, 201*b*, . . . is assumed to be set to the information processing apparatus in advance.

At this time, since the aroma chemical carrier 200 is in such a state that it is biased upwardly together with the pressing body 131 by the elastic body 132, if the user closes the hinge 101, then the aroma chemical fixation portions 201*a*, 201*b*, . . . formed on the aroma chemical carrier 200 are placed into a state in which they are contacted by the protrusions 223 formed on the spoke bodies 222 of the respective corresponding action portions 22*a*, 22*b*, . . . .

If the information processing apparatus is instructed, during execution of an application such as, for example, an application of a game, by the application to present an odor to the user, then the information processing apparatus generates, according to the instruction, an instruction for controlling the aroma chemical presentation apparatus 100.

Here, the instruction generated by the information processing apparatus includes driving target specification information that specifies one of the driving units 23*a*, 23*b*, . . . corresponding to one of the action portions 22*a*, 22*b*, . . . that is in contact with any one of the aroma chemical fixation portions 201*a*, 201*b*, . . . which contains the aroma chemical of the odor to be presented, and driving time information that specifies driving time.

The control circuit unit 30 of the aroma chemical presentation apparatus 100 of the present embodiment accepts this instruction from the information processing apparatus and repeats a reciprocating rotary motion of rotating the specified one of the driving units 23*a*, 23*b*, . . . by five degrees in a predetermined direction and then rotating the specified one driving unit 23*a*, 23*b*, by four degrees in the opposite direction during designated duration or by a designated number of times. Further, the control circuit unit 30 causes the derivation fan 24*a* to rotate to generate an air flow to be directed from the inside of the aroma chemical presentation apparatus 100 toward the nose of the user.

Here, for example, if it is assumed that the type of aroma chemical to be presented is an aroma chemical fixed to the aroma chemical fixation portion 201*a* (accordingly, the driving target specification information is information that specifies the driving unit 23*a*) and the rotation duration is two seconds, then the control circuit unit 30 of the aroma chemical presentation apparatus 100 that accepts this instruction from the information processing apparatus selects the driving unit 23*a* and controls the selected driving unit 23*a* to repeat, for two seconds (for example, by eight times), a reciprocating rotary motion of rotating the selected driving unit 23*a* by five degrees in the predetermined direction and then rotating the selected driving unit 23*a* by four degrees in the direction opposite to the predetermined direction.

Consequently, the aroma chemical fixation portion 201*a* is physically scratched by the protrusions 223 of the driving unit 23*a* contacting with the aroma chemical fixation portion 201*a*, while keeping the contacting state, and at least part of the aroma chemical microcapsules fixed to the aroma chemical fixation portion 201*a* are crushed for 12 times such that the aroma chemical encapsulated in the inside of the aroma chemical microcapsules is emitted.

The emitted aroma chemical is derived from within the aroma chemical presentation apparatus 100 to the nose of the user by an air flow generated by the derivation fan 241*a*. The odor of the aroma chemical emitted is presented to the user in this manner.

[Deodorization] Further, if the information processing apparatus thereafter receives an instruction by the application such as a game to stop the presentation of the odor to the user, then the information processing apparatus generates an instruction for controlling the aroma chemical presentation apparatus 100, according to the received instruction.

The generated instruction is outputted as an instruction for deodorization to the control circuit unit 30 of the aroma chemical presentation apparatus 100. When the control circuit unit 30 of the aroma chemical presentation apparatus 100 receives the instruction for deodorization, the control circuit unit 30 causes the derivation fan 241*a* to step (and it causes, when any driving unit 23 is operating, the driving unit 23 to stop its operation) and causes the exhaust fan 241*b* to rotate. Thus, an air flow directed in a direction opposite to the nose of the user from the inside of the aroma chemical presentation apparatus 100 is generated. Consequently, the emitted aroma chemical that remains in the inside of the aroma chemical presentation apparatus 100 is exhausted in the direction opposite to the nose of the user.

It is to be noted that, in a case where an instruction to present an aroma chemical of a type different from that of the aroma chemical instructed to present in the preceding operation cycle is received from the information processing apparatus, that is, in a case where driving target specification information that specifies a driving unit 23 different from the driving unit 23 specified by the driving target specification information included in the instruction inputted in the preceding operation cycle is inputted, the control circuit unit 30 first causes the derivation fan 241*a* to stop as an operation for deodorization (and causes, when a driving unit 23 is operating, the driving unit 23 to stop its operation) and then causes the exhaust fan 241*b* to rotate.

Then, after exhaustion for a predetermined period of time by the exhaust fan 241*b*, the control circuit unit 30 causes the exhaust fan 241*b* to stop, controls the driving unit 23 specified by the information of the instruction, to perform a reciprocating rotary motion of the driving unit 23, and causes the derivation fan 241*a* to rotate to generate an air flow directed in a direction from the inside of the aroma chemical presentation apparatus 100 toward the nose of the user.

Since the control circuit unit 30 performs such control as described above, mixture of odors is suppressed. However, in a case where it is instructed to intentionally mix a plurality of types of aroma chemicals (in a case where a plurality of driving units 23 are specified by the driving target specification information or in a like case), the control circuit unit 30 controls, at a time, the plurality of driving units 23 specified by the driving target specification information to individually perform a reciprocating rotary motion of the driving units 23 and causes the derivation fan 241*a* to rotate to generate an air flow directed in the direction from the inside of the aroma chemical presentation apparatus 100 toward the nose of the user.

[Control of emission amount of aroma chemical] In the foregoing description, the control circuit unit 30 receives a designation of duration of rotation, the number of times of rotation, and so forth and performs control for repeating a reciprocating rotary motion of rotating one of the driving units 23*a*, 23*b*, . . . specified by the instruction by F degrees in a predetermined direction and rotating the specified one of the driving units 23*a*, 23*b*, . . . by B degrees in the opposite direction to the predetermined direction during the designated duration or by the designated number of times of rotation. However, it possibly occurs that, depending upon a type of aroma chemical, the odor may be strong or weak in comparison with a different type of aroma chemical.

Therefore, in an example of the present embodiment, the control circuit unit 30 may accept settings of rotation amounts F and B ($F>B>0$) in one reciprocation for each of the driving units 23*a*, 23*b*, . . . according to an instruction inputted from the information processing apparatus in advance. For example, the information processing apparatus may set the rotation amounts in one reciprocation of the driving unit 23*a* to $F=3$ degrees and $B=2$ degrees and set the rotation amounts in one reciprocation of the other driving units 23*b*, 23*b*, . . . to $F=5$ degrees and $B=4$ degrees. It is to be noted that, in any setting, the magnitude $\Delta$ of $F-B$ may be fixed. In this case, the information processing apparatus may set one of F and B, and the control circuit unit 30 may set the other one of F and B by performing calculation using $\Delta$ determined in advance.

[Movement in one direction] Further, although the description above is such that, when controlling the driving unit 23, the control circuit unit 30 causes the driving unit 23 to perform a reciprocating rotary motion, the control circuit unit 30 may set B to $B=0$ (that is, not for a reciprocating motion but for a one-way motion). In this case, the control circuit unit 30 accepts only one setting of the rotation amount F ($F-B$ is not necessarily fixed) from the information processing apparatus.

[Recognition of aroma chemical] Further, the aroma chemical presentation apparatus 100 of the present embodiment may include a code image reader that reads, when the aroma chemical carrier 200 is accommodated into the tray unit 10 and then the tray unit 10 is closed, a code image (a bar code, a two-dimensional bar code, or some other computer-readable image) formed at a predetermined location of the aroma chemical carrier 200 and that outputs the read data to the information processing apparatus or the like.

In this example, a code that differs depending upon a type of aroma chemical (or combination of aroma chemicals) formed on the aroma chemical carrier 200 is allocated in advance, and a code image corresponding to the code is formed at a predetermined position of the aroma chemical carrier 200. This makes it possible for the information processing apparatus or the like to acquire information relating to the type of aroma chemical on the aroma chemical carrier 200 set to the aroma chemical presentation apparatus 100.

It is to be noted that the information that associates a code and a type of aroma chemical may be registered in advance in a server not depicted or the like such that the information processing apparatus acquires the information by inquiring the server or the like through a network or the like. Further, with this information, not only information relating to a type of aroma chemical but also information relating to a strength of an odor for each aroma chemical (information relating to an angle to be scratched all at once or the like) may be associated. This makes it possible for the information processing apparatus to issue an instruction for control corresponding to the set aroma chemical carrier 200.

REFERENCE SIGNS LIST

100: Chemical presentation apparatus
200: Aroma chemical carrier
10: Tray unit
11: Bottom portion
12: Wall portion
13: Biasing unit
20: Mechanism unit
21: Mechanism unit housing
22: Action portion
23: Driving unit
24: Air flow controlling unit
30: Control circuit unit

The invention claimed is:

1. An aroma chemical presentation apparatus comprising:
an encapsulation body supporting unit configured for supporting an aroma chemical encapsulation body in which an aroma chemical material is encapsulated;
an action body configured for physically acting upon the aroma chemical encapsulation body to cause the aroma chemical material in the aroma chemical encapsulation body to be emitted; and
a derivation fan configured for forming an air flow in a predetermined direction for deriving the emitted aroma chemical material, and
a control circuit unit configured for controlling operations of the action body to physically contact the aroma chemical encapsulation body to adjust an intensity of odor of the aroma chemical material as emitted,
wherein the operations of the action body comprise duration of rotation of the action body, number of rotations of the action body, a first rotation angle in a first direction and a second rotation angle in a second direction in a repeated reciprocating rotary motion of the action body, and a number of reciprocating motions of the action body.

2. The aroma chemical presentation apparatus according to claim 1, further comprising: an exhaust fan that exhausts the emitted aroma chemical material in a direction different from the predetermined direction of an air flow formed by the derivation fan.

3. The aroma chemical presentation apparatus according to claim 1, further comprising: a driving unit that causes the encapsulation body supporting unit and the action body to move relative to each other.

4. The aroma chemical presentation apparatus according to claim 3, wherein the driving unit causes, when an aroma chemical is to be emitted, the encapsulation body supporting unit and the action body to move relative to each other.

5. The aroma chemical presentation apparatus according to claim 3, wherein:
the aroma chemical encapsulation body is configured to support a plurality of types of aroma chemicals thereon such that each one of the plurality of types of aroma chemicals is individually encapsulated at a predetermined portion of the aroma chemical encapsulation body, and
the control circuit unit is further configured for:
selecting at least one of the plurality of types of aroma chemicals, and
causing the driving unit to drive the action body to physically act upon the aroma chemical encapsulation body to cause the at least one of the plurality of types of aroma chemicals to be emitted.

6. The aroma chemical presentation apparatus according to claim 1, wherein:
the encapsulation body supporting unit includes a biasing unit comprising:
a pressing body disposed in contact with the aroma chemical encapsulation body, and
an elastic body configured to bias the pressing body toward the action body.

7. The aroma chemical presentation apparatus of claim 1, wherein the action body is configured to contact the aroma chemical encapsulation body and be movable relative to the encapsulation body supporting unit such that the action body scratches the aroma chemical encapsulation body such that the aroma chemical material is emitted.

8. An aroma chemical presentation system comprising:
an aroma chemical carrier on which at least one aroma chemical is encapsulated;
a tray for supporting the aroma chemical carrier thereon;
an action portion configured for physically interacting with the aroma chemical carrier to cause the at least one aroma chemical to be emitted;
a derivation fan for directing the at least one aroma chemical toward a user; and
a control circuit unit configured for controlling operations of the action portion to physically contact the aroma chemical encapsulation body to adjust an intensity of odor of the aroma chemical as emitted,
wherein the operations of the action portion comprise duration of rotation of the action portion, number of rotations of the action portion, a first rotation angle in a first direction and a second rotation angle in a second direction in a repeated reciprocating rotary motion of the action portion, and a number of reciprocating motions of the action portion.

9. The aroma chemical presentation system of claim 8, wherein the action portion is configured to contact the aroma chemical carrier and be movable relative to the tray to cause the action portion to scratch the aroma chemical carrier such that the aroma chemical is emitted.

10. The aroma chemical presentation system of claim 8, wherein the tray comprises:
a pressing body in contact with the aroma chemical carrier, and
at least one elastic body configured to bias the pressing body and the aroma chemical carrier toward the action portion.

11. An aroma chemical presentation apparatus comprising:
an encapsulation body supporting unit configured for supporting an aroma chemical encapsulation body in which an aroma chemical material is encapsulated;
an action body configured for physically acting upon the aroma chemical encapsulation body to cause the aroma chemical material in the aroma chemical encapsulation body to be emitted; and a derivation fan configured for forming an air flow in a predetermined direction for deriving the emitted aroma chemical material, and a control circuit unit configured for controlling operations of the action body to adjust an intensity of odor of the aroma chemical material as emitted, wherein the operations of the action body comprise duration of rotation of the action body, number of rotations of the action body, a first rotation angle in a first direction and a second rotation angle in a second direction in a repeated reciprocating rotary motion of the action body, and a number of reciprocating motions of the action body.

12. The aroma chemical presentation apparatus of claim 11, further comprising: an exhaust fan that exhausts the emitted aroma chemical material in a direction different from the predetermined direction of an air flow formed by the derivation fan.

13. The aroma chemical presentation apparatus of claim 11, further comprising: a driving unit that causes the encapsulation body supporting unit and the action body to move relative to each other.

14. The aroma chemical presentation apparatus of claim 13, wherein the driving unit causes, when an aroma chemical is to be emitted, the encapsulation body supporting unit and the action body to move relative to each other.

15. The aroma chemical presentation apparatus of claim 13, wherein:

the aroma chemical encapsulation body is configured to support a plurality of types of aroma chemicals thereon such that each one of the plurality of types of aroma chemicals is individually encapsulated at a predetermined portion of the aroma chemical encapsulation body, and the control circuit unit is further configured for:

selecting at least one of the plurality of types of aroma chemicals, and causing the driving unit to drive the action body to physically act upon the aroma chemical encapsulation body to cause the at least one of the plurality of types of aroma chemicals to be emitted.

16. The aroma chemical presentation apparatus of claim 11, wherein:

the encapsulation body supporting unit includes a biasing unit comprising:

a pressing body disposed in contact with the aroma chemical encapsulation body, and an elastic body configured to bias the pressing body toward the action body.

17. The aroma chemical presentation apparatus of claim 11, wherein the action body is configured to contact the aroma chemical encapsulation body and be movable relative to the encapsulation body supporting unit such that the action body scratches the aroma chemical encapsulation body such that the aroma chemical material is emitted.

* * * * *